United States Patent
Glazer et al.

(10) Patent No.: US 12,322,134 B2
(45) Date of Patent: Jun. 3, 2025

(54) INFANT HEIGHT ESTIMATION

(71) Applicant: UDISENSE INC., New York, NY (US)

(72) Inventors: Assaf Glazer, Kiryat-Ono (IL); Tor Ivry, Rishon Lezion (IL); Amnon Karni, New York, NY (US); Dror Porat, Haifa (IL); Yanai Victor Ankri, Netanya (IL); Sivan Hurvitz, Ramat Gan (IL); Natalie Barnett, New York, NY (US)

(73) Assignee: UdiSense Inc., New York, NY (US)

( * ) Notice: Subject to any disclaimer, the term of this patent is extended or adjusted under 35 U.S.C. 154(b) by 0 days.

(21) Appl. No.: 18/391,689

(22) Filed: Dec. 21, 2023

(65) Prior Publication Data

US 2024/0177344 A1 May 30, 2024

Related U.S. Application Data

(60) Division of application No. 17/381,254, filed on Jul. 21, 2021, now Pat. No. 11,928,839, which is a
(Continued)

(51) Int. Cl.
*G06T 7/73* (2017.01)
*A61B 5/107* (2006.01)
(Continued)

(52) U.S. Cl.
CPC .............. *G06T 7/74* (2017.01); *A61B 5/1079* (2013.01); *G01C 11/04* (2013.01); *G06T 7/62* (2017.01); *G06V 10/462* (2022.01); *G06V 20/52* (2022.01); *G06V 40/10* (2022.01); *G06V 40/103* (2022.01); *A61B 5/4806* (2013.01);
(Continued)

(58) Field of Classification Search
CPC ... G06T 7/74; G06T 7/62; G06T 2207/10016; G06T 2207/30196; G06T 2207/30204; A61B 5/1079; A61B 5/4806; A61B 2503/04; A61B 2560/0223; G01C 11/04;
(Continued)

(56) References Cited

U.S. PATENT DOCUMENTS

| 10,470,584 B2 * | 11/2019 | Woolfson | A47C 31/123 |
| 2013/0195330 A1 * | 8/2013 | Kim | G06V 40/10 |
| | | | 382/128 |

(Continued)

FOREIGN PATENT DOCUMENTS

| CN | 1105336474 A | 12/2019 |
| WO | 2005116924 A1 | 12/2005 |
| WO | 2017099598 A1 | 6/2017 |

OTHER PUBLICATIONS

CN Application # 202080066623.2 Office Action dated Sep. 23, 2004.
(Continued)

*Primary Examiner* — Amara Abdi
(74) *Attorney, Agent, or Firm* — Meitar Patents Ltd.; Daniel Kligler

(57) ABSTRACT

A method for photogrammetric measurement includes capturing a sequence of images of an infant lying in a crib and processing the images so as to extract a skeleton of the infant from one or more of the images. A height of the infant is estimated based on the extracted skeleton.

15 Claims, 7 Drawing Sheets

Related U.S. Application Data continuation of application No. PCT/US2020/066288, filed on Dec. 21, 2020.

(60) Provisional application No. 62/963,042, filed on Jan. 19, 2020.

(51) Int. Cl.
| | | |
|---|---|---|
| *G01C 11/04* | (2006.01) | |
| *G06T 7/62* | (2017.01) | |
| *G06V 10/46* | (2022.01) | |
| *G06V 20/52* | (2022.01) | |
| *G06V 40/10* | (2022.01) | |
| *A61B 5/00* | (2006.01) | |

(52) U.S. Cl.
CPC ... *A61B 2503/04* (2013.01); *A61B 2560/0223* (2013.01); *G06T 2207/10016* (2013.01); *G06T 2207/30196* (2013.01)

(58) Field of Classification Search
CPC ...... G06V 10/462; G06V 20/52; G06V 40/10; G06V 40/103
See application file for complete search history.

(56) References Cited

U.S. PATENT DOCUMENTS

| | | | |
|---|---|---|---|
| 2013/0256411 | A1 | 10/2013 | Schuler |
| 2014/0300722 | A1* | 10/2014 | Garcia .................. G01B 11/02 348/135 |
| 2015/0022637 | A1* | 1/2015 | Saeki .................... G06T 7/0004 348/46 |
| 2016/0012611 | A1 | 1/2016 | Wexler et al. |
| 2016/0342830 | A1* | 11/2016 | Ariizumi ................ G06V 20/64 |
| 2018/0035082 | A1* | 2/2018 | Patil ......................... A61B 5/45 |
| 2018/0360393 | A1* | 12/2018 | Van Berkel-Wijnen ..................... A61B 5/1079 |
| 2019/0066327 | A1* | 2/2019 | Fujimoto .................. G06T 7/60 |
| 2020/0258257 | A1* | 8/2020 | Shimoyama .............. G06T 7/97 |
| 2020/0268172 | A1* | 8/2020 | El Mali ................ A61B 5/6891 |

OTHER PUBLICATIONS

CN Application # 202080066623.2 Office Action dated Feb. 13, 2025.

* cited by examiner

INFANT HEIGHT ESTIMATION

CROSS-REFERENCE TO RELATED APPLICATION

This application is a division of U.S. patent application Ser. No. 17/381,254, filed Jul. 21, 2021, which is a continuation of PCT Patent Application PCT/US2020/66288, filed Dec. 21, 2020, which claims the benefit of U.S. Provisional Patent Application 62/963,042, filed Jan. 19, 2020, which is incorporated herein by reference.

FIELD OF THE INVENTION

The present invention relates generally to image processing, and particularly to apparatus, systems and methods for measuring a human subject.

BACKGROUND

PCT International Publication WO 2017/196695, whose disclosure is incorporated herein by reference, describes a video monitoring system, which includes a camera head, including an infrared illumination source and an image sensor. A mount is configured to hold the camera head in a fixed location and orientation above a crib, so that the image sensor captures images of the crib and an intervention region adjacent to the crib from a fixed perspective.

U.S. Patent Application Publication 2019/050798, whose disclosure is incorporated herein by reference, describes a system for respiration monitoring in which a garment is fitted snugly around a body of a human subject, and includes, on at least a portion of the garment that fits around a thorax of the subject, a pattern of light and dark pigments having a high contrast at a near infrared wavelength. A camera head is mounted in proximity to a bed in which the subject is to be placed, and includes an image sensor and an infrared illumination source, which is configured to illuminate the bed with radiation at the near infrared wavelength, and is configured to transmit a video stream of images of the subject in the bed captured by the image sensor to a processor, which analyzes movement of the pattern in the images in order to detect a respiratory motion of the thorax.

SUMMARY

Embodiments of the present invention that are described hereinbelow provide systems and methods for photogrammetric measurement.

There is therefore provided, in accordance with an embodiment of the invention, a method for photogrammetric measurement, which includes providing a bedsheet having one or more patterns printed thereon in accordance with a pattern template, which defines respective locations of the one or more patterns in a template coordinate frame. An image is received, in an image coordinate frame, of a person lying on a bed, which is covered by the bedsheet. The image is processed in order to identify the one or more patterns in the image and to match the one or more patterns identified in the image to the one or more patterns in the pattern template. A transformation is computed, based on the matched patterns, between the image coordinate frame and the template coordinate frame. A dimension of the person is measured by applying the computed transformation to the image of the person.

In a disclosed embodiment, the person is an infant, and the bed is a crib.

In some embodiments, the one or more patterns include a plurality of different patterns, which are printed in different, respective corners of the bedsheet. Additionally or alternatively, the one or more patterns includes an arrangement of light or dark geometrical shapes, with high contrast between light and dark parts of the pattern.

In a disclosed embodiment, processing the image includes comparing the one or more patterns identified in the image to a library of pattern templates, and selecting the pattern template from the library that matches the one or more patterns identified in the image.

In some embodiments, processing the image includes identifying key points in the one or more patterns, detecting features associated with the key points, and matching the features to the pattern template. In the disclosed embodiments, the one or more patterns each include multiple components, and detecting the features includes analyzing the image so as to compute geometrical characteristics of the components. The geometrical characteristics are selected, for example, from a set of characteristics consisting of a symmetry of the components, a number of the components, a proportion of the components, an aspect ratio of the components, a density of the components, a concavity of the components, linear features of the components, and textural features of the components.

Typically, computing the transformation includes compensating for a scale and a distortion of the image.

In a disclosed embodiment, measuring the dimension includes computing at least one measurement selected from a set of measurements consisting of a length of the body of the person and a circumference of a head of the person. Alternatively or additionally, measuring the dimension includes identifying locations of landmarks along a body of the person in the image, and computing distances between the identified locations.

In some embodiments, measuring the dimension includes detecting a shrinkage of the bedsheet, computing a calibration factor to correct for the shrinkage, and correcting the measured dimension using the calibration factor. In one embodiment, computing the calibration factor includes displaying a calibration target on a screen of a client device that is placed on the bed, capturing a calibration image of bedsheet with the calibration target, and processing the calibration image in order to find the calibration factor.

There is also provided, in accordance with an embodiment of the invention, a system for photogrammetric measurement, including a bedsheet having one or more patterns printed thereon in accordance with a pattern template, which defines respective locations of the one or more patterns in a template coordinate frame. A camera is configured to capture an image, in an image coordinate frame, of a person lying on a bed, which is covered by the bedsheet. A processor is configured to process the image in order to identify the one or more patterns in the image, to match the one or more patterns identified in the image to the one or more patterns in the pattern template, to compute a transformation, based on the matched patterns, between the image coordinate frame and the template coordinate frame, and to measure a dimension of the person by applying the computed transformation to the image of the person.

There is additionally provided, in accordance with an embodiment of the invention, a bedsheet having a plurality of different patterns printed thereon with a high contrast in different, respective corners of the bedsheet in accordance with a predefined pattern template.

In a disclosed embodiment, each of the patterns includes an arrangement of light or dark geometrical shapes, while a remainder of an area of the bedsheet outside the patterns in the corners is unpatterned or has a low-contrast pattern.

There is further provided, in accordance with an embodiment of the invention, a method for photogrammetric measurement, which includes capturing a sequence of images of an infant lying in a crib. The images are processed so as to extract a skeleton of the infant from one or more of the images. A height of the infant is estimated based on the extracted skeleton.

In a disclosed embodiment, processing the images includes selecting one or more of the images within the sequence that are appropriate for height measurement, and eliminating the images that are not appropriate.

Additionally or alternatively, estimating the height includes measuring and summing distances in the images between joints of the skeleton. In one embodiment, estimating the height includes extracting respective height measurements from a plurality of the images, and outputting a largest value among the height measurements as the height of the infant.

There is moreover provided, in accordance with an embodiment of the invention, a computer software product, including a computer-readable medium in which program instructions are stored, which instructions, when read by a computer, cause the computer to capture a sequence of images of an infant lying in a crib, to process the images so as to extract a skeleton of the infant from one or more of the images, and to estimate a height of the infant based on the extracted skeleton.

The present invention will be more fully understood from the following detailed description of the embodiments thereof, taken together with the drawings in which:

DETAILED DESCRIPTION OF EMBODIMENTS

The above-referenced PCT International Publication WO 2017/196695 and U.S. Patent Application Publication 2019/050798 describe cameras and systems that can be used to monitor movement, behavior and respiration of a small child (or other subject) in a crib or other bed. These systems are useful in detecting health emergencies, such as respiratory arrest, as well as in assisting in the development of good sleeping habits.

In addition to these sorts of nightly monitoring applications, many parents are also interested in monitoring the growth of their child over periods of weeks and months. Manual measurements, however, for example using a tape measure, tend to be inaccurate. Measurements can also be made by computerized processing of video images of the child, but the accuracy of these measurements is strongly affected by variations in the distance and perspective angle of the camera from the subject, as well as by the child's posture while sleeping (which only rarely forms a straight line from head to feet).

Embodiments of the present invention address these problems by using specially-designed bedsheets as a calibration template for photogrammetric measurements of the child. The bedsheets are imprinted or otherwise decorated with known patterns in multiple locations, for example at the corners of the bed. A camera, such as a dedicated monitoring camera or a handheld device (for example, a smartphone camera), captures images of a child or other subject lying on a bedsheet of this sort. A computer or other processor processes one or more of the images in order to detect the patterns and identify precisely their respective positions (locations and orientations) in the image. Based on these positions, the processor computes a transformation between the pixel coordinates in the image and the precise, geometrical coordinates of the bedsheet. This scheme enables the processor to compensate even for highly-angled images, with variable points of view, that can arise when the images are captured by a handheld device.

By applying this transformation to the body of the child appearing in the image, the processor is able to measure the body dimensions accurately and report features such as the length, width and circumference of the body and of parts of the body, such as the head, as well as estimating the child's weight and body mass index (BMI). For more precise measurement, the processor may identify the locations of joints and other key landmarks in the child's body, either automatically or with user assistance in marking these locations in an image. The processor then computes the distances between these locations and uses the distances in measuring the body dimensions.

Figure 1:
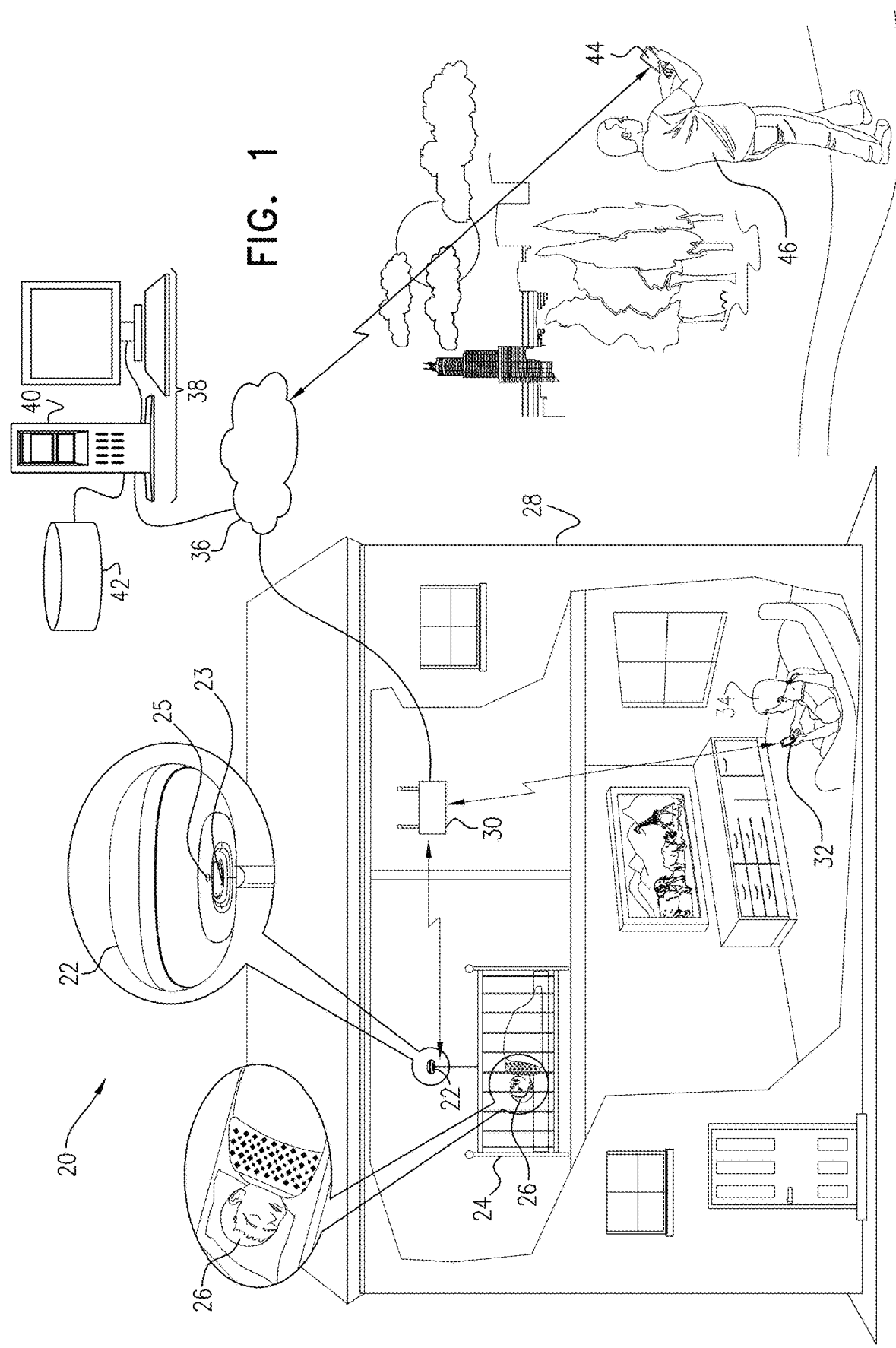
FIG. 1 is a block diagram that schematically illustrates a system for infant sleep monitoring and measurement, in accordance with an embodiment of the invention.

FIG. 1 is a block diagram that schematically illustrates a system 20 for infant sleep monitoring, in accordance with an embodiment of the invention. System 20 comprises a monitoring camera head 22, which is mounted above a crib 24, in which an infant 26 is sleeping in a residence 28. Alternatively, camera head 22 may be mounted in another suitable location in proximity to the crib, mounted on a wall or tabletop, for example. Further alternatively, as noted earlier, some of the functionalities of camera head 22 may be carried out using a handheld camera (not shown) with suitable communication capabilities, such as the camera in a smartphone.

For purposes of image capture in the pictured system, an infrared (IR) light-emitting diode (LED) 25 on the lower side of camera head 22 illuminates the sleeping infant 26. A diffuser can be used to spread the infrared light uniformly across the crib. Camera head 22 also comprises an infrared-sensitive image sensor 23. The resolution and sensitivity of image sensor 23 can be optimized for night conditions, and specifically for the wavelength range of LED 25. Further details of camera head 22, including its internal components and modes of operation, are described in the above-mentioned PCT International Publication WO 2017/196695

(particularly in FIGS. 4A/B and 5 and the corresponding description in the specification on pages 8-9). This PCT publication also describes different ways of mounting the camera head above or alongside the crib.

Camera head 22 transmits digitized streaming video, and possibly other signals, as well, over a local network to a router 30, typically via a wireless local area network (LAN) link, such as a Wi-Fi connection, or a wired link, such as an Ethernet connection. Camera head 22 transmits the digitized video data in packets that are addressed so that router 30 forwards the video packets to either or both of a local client device 32 on the local network and a remote server 38 via a public network 36, such as the Internet. Client device 32 typically comprises a smartphone, tablet or personal computer, which enables a caregiver 34 in another room of residence 28 to monitor infant 26, even when there is no Internet connection available. Server 38 makes video images and other data available to authorized remote client devices 44, thus enabling a caregiver 46 to monitor infant 26 at any location where there is access to public network 36. The Wi-Fi or other local network connection provides reliable video streaming from camera head 22 to client device 32 with high bandwidth and low latency, even if the external Internet connection is not working. As long as the Internet is connected, however, the video stream is also transmitted to server 38 for purposes of analysis and retransmission.

Server 38 typically comprises a general-purpose computer, comprising a processor 40 and a memory 42, which receives, stores and analyzes images from camera head 22 in residence 28 and similarly from other cameras in other residences (not shown). In the present embodiment, processor 40 analyzes the images in order to make photogrammetric measurements of infant 26, as described further hereinbelow. In addition, processor may detect and measure respiratory motion of the thorax of infant 26, and may thus provide caregivers 34 and 46 with reports and (when required) alerts regarding the infant's breathing patterns, as described in the above-mentioned U.S. Patent Application Publication 2019/050798. Processor 40 typically performs these functions under the control of software, which may be downloaded to server 38 in electronic form, over a network, for example, as well as stored on tangible, non-transitory computer-readable media, such as magnetic, optical or electronic memory media. Alternatively or additionally, some or all of these processing, measurement and monitoring functions may be performed locally, for example by a microprocessor in camera head 22 and/or by suitable application software running on processors in client devices 32 and/or 44.

Figure 2:
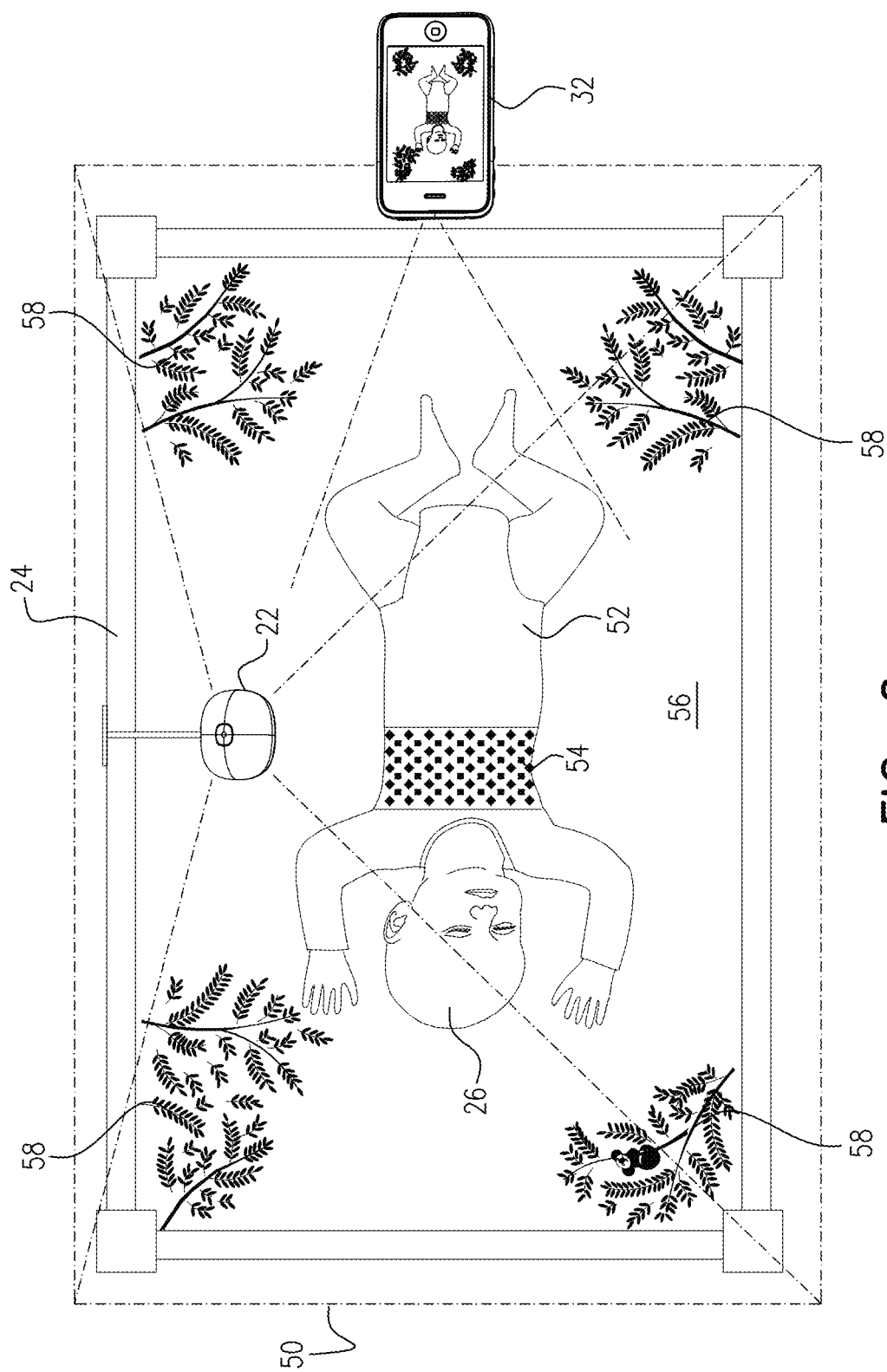
FIG. 2 is a schematic top view of a camera head mounted over an infant's crib, in accordance with an embodiment of the invention.

FIG. 2 is a schematic top view showing details of the deployment and use of monitoring camera head 22 over crib 24, in accordance with an embodiment of the invention. In the pictured embodiment, for purposes of respiration monitoring (as described in the above-mentioned U.S. Patent Application Publication 2019/050798), infant 26 in crib 24 is wearing a garment 52, such as pajamas or a swaddling sack, with a periodic pattern printed on a portion 54 of the garment that fits around the infant's thorax. Crib 24 is covered with a special-purpose bedsheet 56, with patterns 58 having predefined, distinguishable forms printed on the corners of the bedsheet in predefined locations, in order to serve as a calibration template for photogrammetric measurements of infant 26. In the present example, patterns 58 are chosen specifically so as to be clearly distinguishable from the patterns on garment 52.

In the pictured embodiment, monitoring camera head 22 stands against a wall over crib 24. Camera head 22 is held, for example, at the end of an arm at the upper end of a tripod mount behind crib 24, at the midpoint of the long side of the crib. Camera head 22 in this embodiment is positioned and adjusted so that the camera head has a field of view 50 from a perspective that encompasses all or most of the area of crib 24. This perspective provides server 38 with image information that can be analyzed conveniently and reliably.

Alternatively, the camera head may be mounted in any other suitable location in proximity to crib 24; or a handheld camera may be used, as noted above. For example, as shown in FIG. 2, a smartphone, such as client device 32, may be used to capture images of crib 24 and infant. In the pictured example, client device 32 captures an image from a location on the short side of crib 24, from a high angle. The methods of transformation and measurement that are described herein may be applied to such images, as well.

Figure 3:
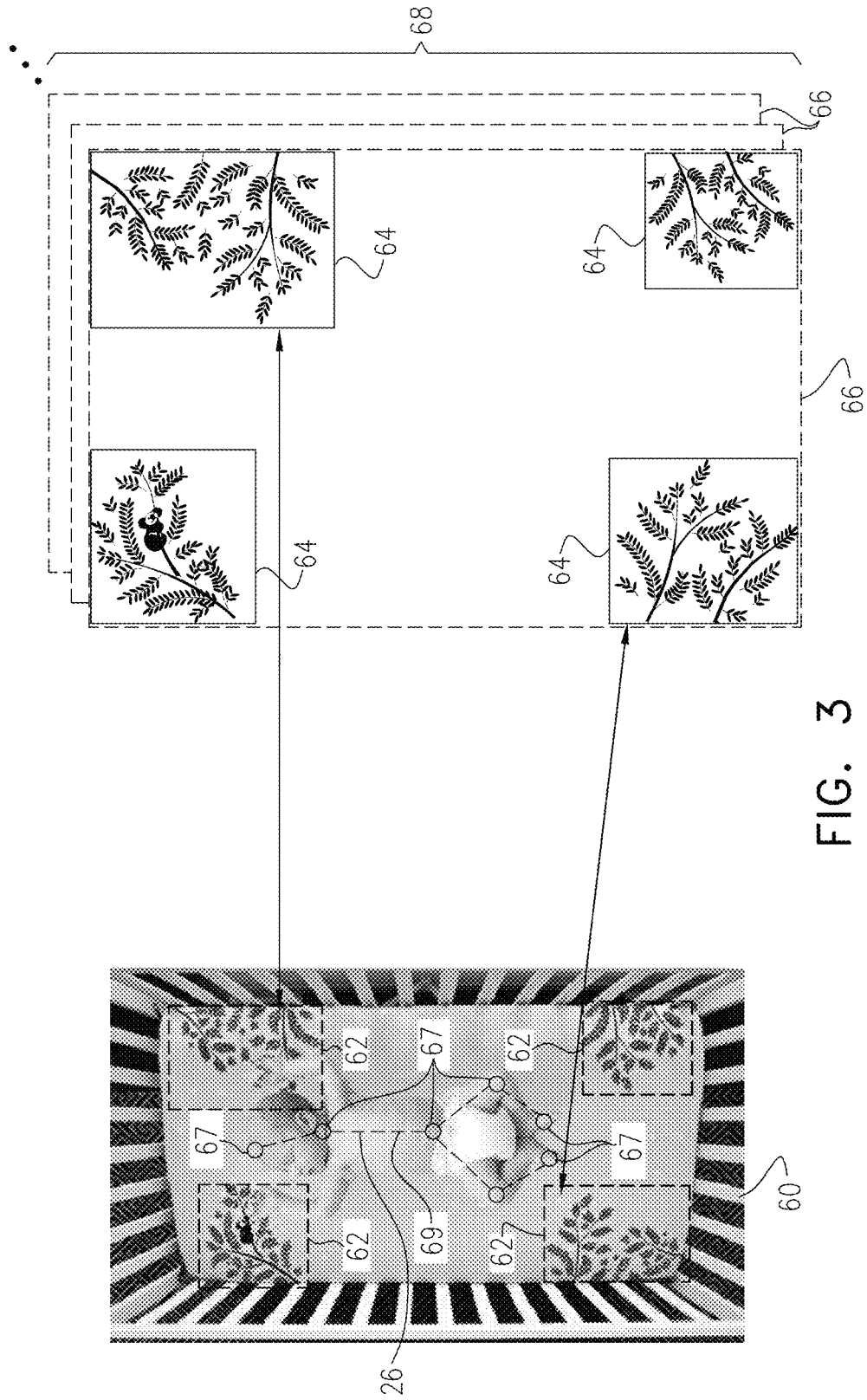
FIG. 3 is a schematic representation of an image captured by the camera head of FIG. 2, illustrating a method for mapping patterns in the image to a calibration template, in accordance with an embodiment of the invention.

FIG. 3 is a schematic representation of an image 60 captured by camera head 22, illustrating a method for mapping patterns 62 in the image to a calibration template 66, in accordance with an embodiment of the invention. Image 60 is distorted as a result of the off-center camera location and perspective angle. The distortion is reflected in corresponding changes in the locations and shapes of patterns 62 in image 60.

Server 38 (FIG. 1) receives and processes image 60 in order to map patterns 62 on the bedsheet in image 60 to corresponding patterns 64 of calibration template 66, in accordance with an embodiment of the invention. Assuming multiple different styles of patterned bedsheets are deployed in different user premises, server 38 maintains a library 68 of templates 66 in memory 42, with each template containing patterns 64 belonging to a different style. The pattern features can be stored in memory 42 in a suitable data structure, such as a database, to enable processor 40 to efficiently sort and choose the appropriate template for each image 60. For purposes of pattern matching, features of patterns 64 in calibration template 66 can be stored in a suitable data structure, such as a database, in memory 42, for example in the form of feature vectors, in which the features correspond to the key points in each pattern. Alternatively, processor 40 may extract key points from image 60 and then process templates 66 in order to find and select the template that most closely matches image 60.

Patterns 62 are chosen to include a large number of unique key points, in order to facilitate their identification by processor 40. In the pictured examples, the key points have the form of corners, i.e., intersection points of straight or curved edges in the patterns. Such key points can be identified in terms of their respective coordinates in the image, as well as the angle between the corresponding intersecting edges. Each of patterns 62 and the corresponding pattern 64 have a different, distinct set of key points, thus enabling processor 40 to distinguish readily between the patterns in image 60. It is generally desirable that the arrangements of key points in the patterns be irregular, i.e., not periodic, in order to reduce the likelihood of errors in pattern matching.

In the pictured embodiment, patterns 62 comprise an arrangement of light or dark geometrical shapes, with high contrast between them, and are limited to specific, bounded areas, particularly in the corners of the bedsheet. The remainder of the area of the bedsheet is typically unpatterned, or may have a low-contrast pattern that is easily distinguishable from patterns 62. The separation between the areas of patterns 62 is useful in computing a geometric transformation to compensate for the scale and distortion of image 60. Furthermore, the corners of the bedsheet are least likely to be obscured by the infant in the crib. Even if one of the corners is obscured, the patterns in the other corners will be visible in image 60, and processor 40 will be able to compute the transformation on this basis. It is desirable that the patterns in all four corners be unique, with each corner different from all others, in order to avoid false matches and to ensure that the image on the sheet is matched to the appropriate template in the correct orientation.

The geometrical transformation that is computed in this manner assumes that the dimensions of patterns 62 for any given sheet template belonging to library 68 are known and fixed. In practice, there may be some deviation in the dimensions due, for example, to shrinkage of the sheets as the result of laundering. To avoid measurement errors due to these deviations, the dimensions of the patterns on the sheets may be verified and calibrated by placing a calibration target of known, fixed dimensions on the sheet and then capturing and processing an image similar to image 60, but with the calibration target in place of the infant. As one example, the calibration target can be a rectangle, circle or other shape of known size that is drawn on screen by application software running on client device 32. A scheme of this sort is described further hereinbelow with reference to FIGS. 5 and 6. Alternatively, a physical object of known dimensions or with a printed pattern of known dimensions may be used as the calibration target.

In addition to matching image 60 to template 66, processor 40 also identifies locations 67 of joints and other key landmarks in the image of the body of infant 26, and uses these points in constructing a geometrical skeleton 69. (The term "skeleton," as used in the context of the present description and in the claims, refers to a geometrical construct connecting joints and/or other landmarks identified in an image and does not necessarily to correspond to the infant's physiological skeleton.) In the pictured example, locations 67 include the top of the infant's head, the bottom of the infant's neck, the center of the hip, the knees, and the bottoms of the feet. Alternatively or additionally, other points may be identified. Processor 40 may identify locations 67 automatically, using methods of image processing that are known in the art, or with the assistance of a user. For this latter purpose, for example, image 60 may be presented on the touchscreen of client device 32, and the user may be prompted to manually mark the locations on the touchscreen. In either case, processor 40 uses the calibrated lengths of the segments of skeleton 69 in measuring the body dimensions of infant 26. This method of measurement is described further hereinbelow with reference to FIG. 7.

Figure 4:
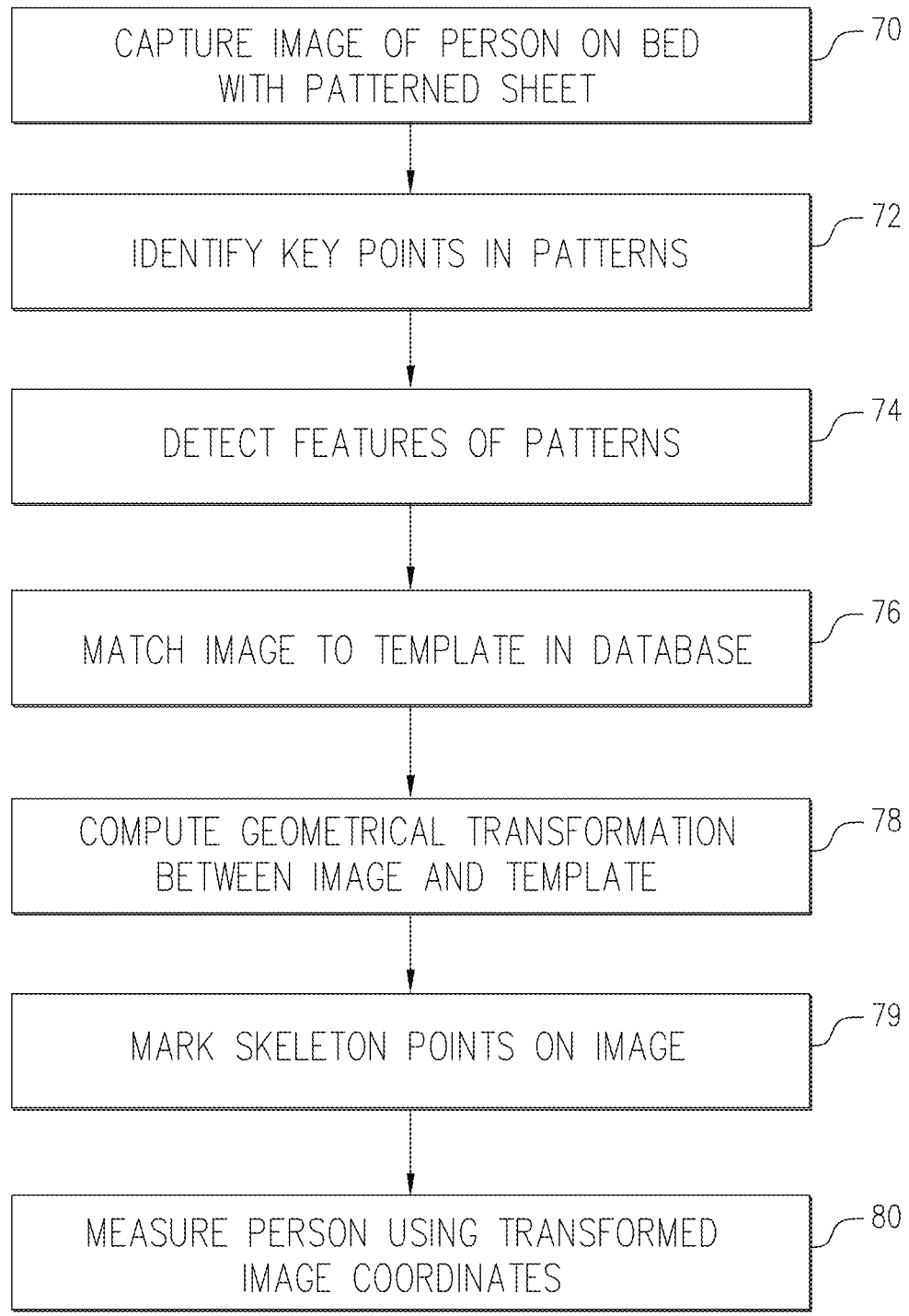
FIG. 4 is a flow chart that schematically illustrates a method for making photogrammetric measurements using a patterned bedsheet for calibration, in accordance with an embodiment of the invention.

FIG. 4 is a flow chart that schematically illustrates a method for making photogrammetric measurements using patterned bedsheet 56 for calibration, in accordance with an embodiment of the invention. The method is described, for the sake of concreteness and clarity, with reference to the elements of system 20 that are shown in FIG. 1 and the features bedsheet 56 and patterns 62 and 64 that are shown in FIG. 3. For enhanced accuracy, the method may optionally be preceded by a calibration procedure, which is described hereinbelow with reference to FIGS. 5 and 6. The principles of the methods of photogrammetric measurement that are described herein may similarly be implemented using other sorts of patterned bedsheets, as well as other cameras and processors for image capture and processing. All such alternative implementations are considered to be within the scope of the present invention.

The method of FIG. 4 is initiated by capturing an image of a person, such as image 60 of infant 26, on a patterned bedsheet, such as bedsheet 56, at an image capture step 70.

To identify patterns 62 in image 60, processor 40 applies a feature detection algorithm to identify key points in the patterns, at a key point identification step 72. For example, processor 40 may apply the scale-invariant feature transform (SIFT) for this purpose. SIFT (and other, similar algorithms) are advantageous in being able to identify key points in patterns 62 notwithstanding changes in scaling, orientation, illumination and distortion in image 60.

Processor 40 searches for candidate patterns 62 in image 60, and then computes a respective feature vector over the key points of these patterns, at a feature detection step 74. Processor 40 compares the feature vectors computed over patterns 62 to those in the database and finds matching patterns 64, typically by computing the Euclidean distances between the feature vectors, at a vector matching step 76. Alternatively or additionally, after extracting the key points of patterns 62 in image 60, processor may search for and extract similar key points from patterns 64 of templates 66 in order to find the matching patterns. Further filtering and confidence testing steps can be used to verify that all of patterns 62 (four patterns in the pictured example) match corresponding patterns 64 of a given template in the database. Alternatively, it may be sufficient that a match is found to a subset of patterns 64 (for example, three out of four patterns), in case one of patterns 62 is occluded by the infant or another object.

Further alternatively, processor 40 may apply other methods of pattern matching that are known in the art in order to match patterns 62 in image 60 to corresponding patterns 64 in sheet templates. For example, the processor may perform a cross-correlation between the patterns in either the spatial domain or frequency domain. As another example, a neural network may be trained to match patterns 62 to templates 66.

Once processor 40 has identified patterns 62 with the corresponding patterns 64 in template 66, the processor computes a geometrical transformation between the coordinates of patterns 62 in image and those of patterns 64 in template 66, in a transformation computation step 78. For example, processor 40 may compute a transformation matrix in homogeneous coordinates, which will project each point in the coordinate frame of image 60 onto a precise Cartesian coordinate frame defined by template 66. This transformation includes scaling and rotational components (similar to an affine transform) in order to compensate for the perspective of camera head 22 and possibly for image distortion due to the camera optics. The coefficients of the transformation matrix can be computed, for example, by an optimization process, in which the coefficients are adjusted until mapping errors of the key points in image 60 are minimized.

For purposes of measuring the body dimensions of infant 26, processor 40 marks locations 67 of points on skeleton 69 that appear in image 60, in a skeleton marking step 79. As explained earlier, this step may be carried out automatically or with user assistance. Additionally or alternatively, processor 40 may identify and analyze other geometrical features in the image of the infant, such as the outline of the infant's head and/or torso, or the location of the infant's hands. Further details of a method that can be applied at this step are described below with reference to FIG. 7.

The Cartesian coordinate frame of template 66 gives a precise linear distance between any two points in the coordinate frame, and thus between any two points in image 60 once the coordinate transformation has been applied. Processor 40 applies this coordinate frame in measuring the dimensions of infant 26, at a photogrammetric measurement step 80. Based on the coordinates (in the transformed coordinate frame) of these features, processor 40 computes measurements such as the length of the infant's body and the circumference of the infant's head. For example, processor 40 may transform the coordinates of locations 67 and then measure and sum the distances along skeleton 69 between the transformed coordinates of these locations in order to find the height of infant 26, irrespective of the infant's sleeping posture. The processor stores the measurements in memory 42 and/or outputs the measurements, for example to client device 32 and/or 44.

Referring back to steps 72 and 74, the task of identifying patterns 62 in image 60 may be complicated by clutter due to other patterned items within crib 24. In the pictured example, the pattern on garment 52 may cause confusion in this regard. Other items, such as garments, blankets and toys, for example, may add to the clutter and lead to erroneous identification of patterns in the image captured at step 70. Such errors will increase the burden on processor 40 and may cause the entire measurement process to fail.

In order to aid processor 40 in distinguishing between patterns 62 and other patterns that may occur within the field of view of camera head 22, the components of patterns 62 could have features with distinct optical and geometrical characteristics. The optical characteristics typically include high contrast between the light and dark parts of the pattern under a wide range of lighting conditions, particularly (but not only) under the infrared illumination provided by the camera head in some embodiments. "High contrast" in this context means that the intensity values of bright pixels within the images of pattern 62 are at least twice those of nearby dark pixels, and possibly even greater, so that the images of the pattern can be readily binarized without loss of detail. Bedsheets 56 may be printed with high-contrast dyes for this purpose. Alternatively or additionally, when measurements can be taken under bright ambient light, color characteristics can be used in identifying patterns 62.

Geometrical characteristics that can be applied in identifying patterns 62 are described further hereinbelow. In one embodiment, processor 40 applies techniques of morphological analysis in order to recognize patterns 62 on the basis of these geometrical characteristics. Additionally or alternatively, processor 40 may apply other methods of image analysis, such as techniques based on deep learning, in recognizing patterns 62.

Examples of geometrical characteristics that can be computed and applied in this regard include:
- Symmetry among the pattern components.
- Numbers of distinct components in each pattern.
- Proportions of the pattern components and/or the overall pattern area.
- Density of the pattern, i.e., the proportion or areas between light and dark parts of the pattern.
- Aspect ratios of the pattern components and/or the overall pattern area.
- Concavity of pattern components, for example based on the ratio of dark to light areas within a convex hull enclosing a connected component of the pattern.
- Linear features of the pattern components and the angles between linear features.
- Textural features of the pattern components.

In some embodiments, such as those illustrated in FIGS. 2 and 3, each of patterns 62 is made up of multiple components in mutual proximity, for example more than twenty separate components, in order to facilitate identification of the patterns by processor 40. Thus, after identifying the candidate components in image 60, the processor may count the number of candidate components in mutual proximity, and identify localized clusters including sufficient numbers of components as candidates to correspond to patterns 62. Processor 40 extracts key points from the components, and compares the sets of key points in each candidate cluster of components to those of templates 66 in memory 42, in order to match the bedsheet in the image to the appropriate template. Calibration and measurement can then proceed, as explained above.

Figure 5:
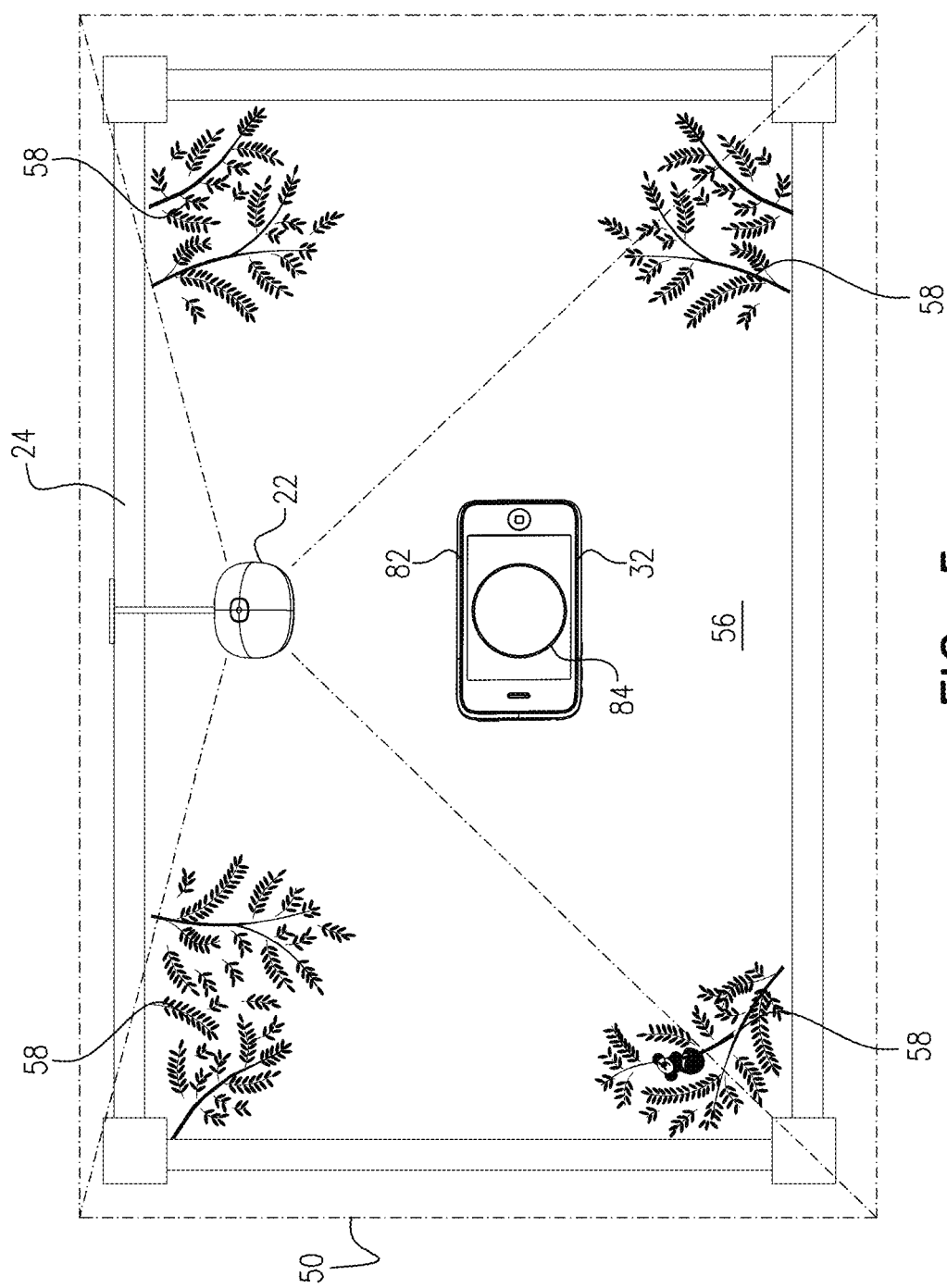
FIG. 5 is a schematic top view of a camera head mounted over an infant's crib in a calibration configuration, in accordance with an embodiment of the invention.
Figure 6:
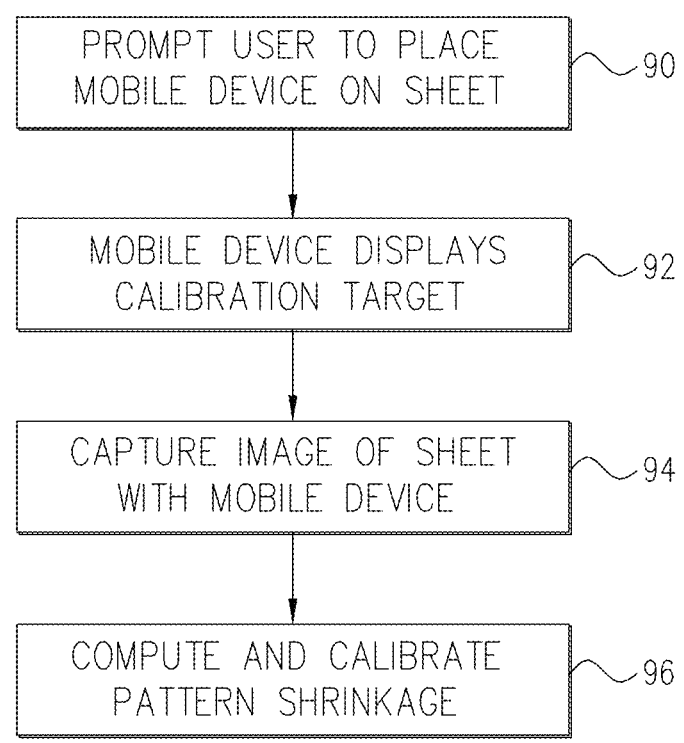
FIG. 6 is a flow chart that schematically illustrates a method for calibration of a patterned bedsheet used in photogrammetric measurements, in accordance with an embodiment of the invention.

Reference is now made to FIGS. 5 and 6, which schematically illustrate method for calibration of a patterned bedsheet used in photogrammetric measurements, in accordance with an embodiment of the invention. FIG. 5 is a schematic top view of crib 24 and camera head 22, with client device 32 placed on sheet 56 and presenting a calibration target 84 on a display screen 82 of the client device. FIG. 6 is a flow chart showing steps in the calibration process. As noted earlier, this method can be used to compensate for changes that can occur in the dimensions of patterns 58 for example due to shrinkage of sheet 56 as the result of laundering. (Although it would be possible to produce sheet 56 from non-shrink fabrics and/or ultra-low shrinkage fabrics, the soft, natural fabrics that are preferred in crib sheets may shrink when laundered.) In an alternative embodiment, as noted above, a physical object can be used as the calibration target.

Caregiver 34 (FIG. 1) runs a measurement application on client device 32. As a part of the set-up procedure, the application prompts caregiver to place client device 32 (or a physical object of a known size) on sheet 56 below camera head 22, at a user prompt step 90. The caregiver indicates to the application that calibration can proceed, for example by pressing a "ready" button on screen 82. The caregiver then withdraws from the field of view of the camera head, and client device 32 displays calibration target 84, at a display step 92. Typically (although not necessarily), the size of calibration target 84 in pixels is set, depending on the characteristics of client device 32 and screen 82, so that the physical dimensions of the calibration target are the same regardless of the type of client device and the dimensions of the screen. For example, server 38 may instruct client device 32 to render the calibration target while taking into account the known pixel size of screen 82, i.e., the dimensions of the calibration target in pixels vary inversely with the pixel size.

Camera head 22 captures an image of sheet 56 including client device 32 in place and calibration target 84 on display 82, at an image capture step 94. Camera head 22 transmits the image to server 38 for analysis. Processor 40 processes the image in order to detect and measure the sizes of both calibration target 84 and patterns 58, at a computation and calibration step 96. The size of the calibration target in the image gives an absolute size reference, against which processor 40 can detect any shrinkage of the patterns on sheet 56, relative to the default dimensions of the pattern, and compute a calibration factor to correct for the shrinkage. Subsequently, at step 80 (FIG. 4), the processor applies this calibration factor to the transformed image coordinates in correcting the measured dimensions of infant 26.

Figure 7:
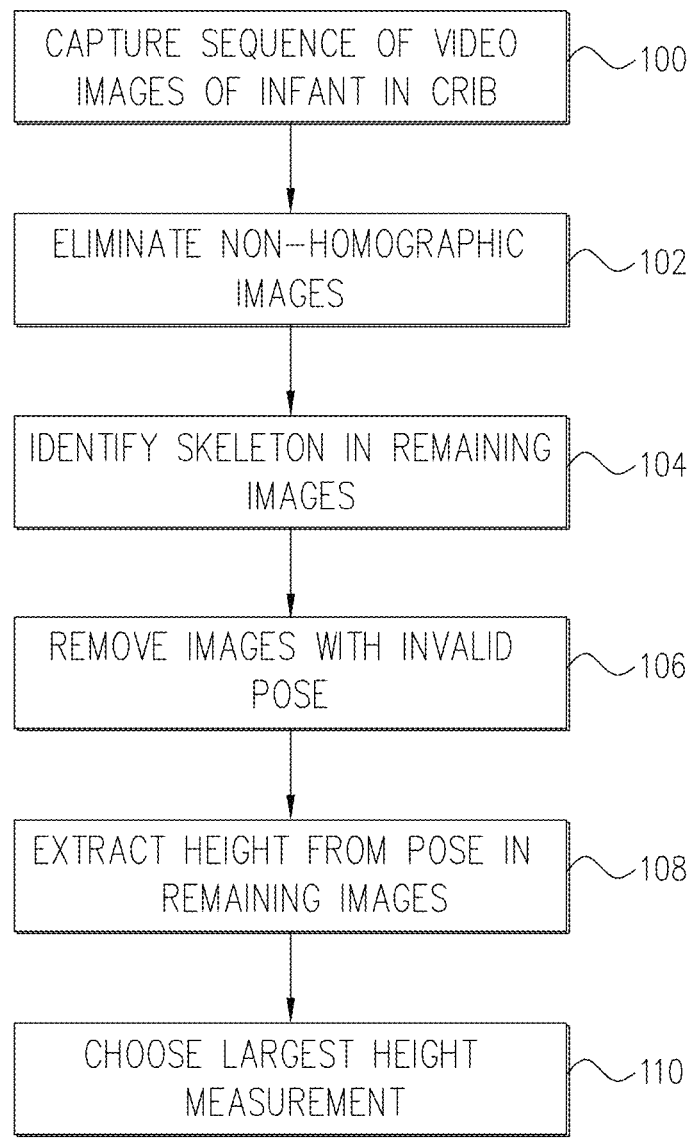
FIG. 7 is a flow chart that schematically illustrates a method for measuring the height of an infant, in accordance with an embodiment of the invention.

FIG. 7 is a flow chart that schematically illustrates a method for measuring the height of infant 26, in accordance with an embodiment of the invention. This method addresses the unique problems that are associated with measuring an infant, who cannot stand up and cannot easily be made to lie still in a supine position. It can advantageously be applied in conjunction with the patterned sheets shown in FIGS. 2 and 3 and the methods of image calibration and transformation that are shown in FIG. 4. Alternatively, the method of FIG. 7 may be applied using other methods of image scale calibration and rectification that are known in the art. The present method can advantageously be applied using a camera that provides a fixed, well-controlled perspective, such as camera head 22 in FIG. 2. Alternatively, this method can also be used in extracting height measurements from images captured using a handheld camera, as in client device 32.

The camera captures a sequence of video images of the infant in a crib, at a sequence capture step 100. Capturing an image sequence, rather than a single still image, is desirable in order to improve the chances of finding an image that will facilitate accurate measurement. A computer, for example server 38 (FIG. 1) or client device 32, processes the images in order to compute the scale and perspective of each image. The computer then applies an appropriate homographic transformation to each image so that all the images are rectified to the same scale and perspective. The transformation may be computed using patterns on a sheet in the infant's crib, as described above. Alternatively, any other method of scale and perspective calibration that is known in the art may be used at this step. The computer eliminates any non-homographic image frames, i.e., frames in which calibration failed (for example because the infant was lying on the pattern used for calibration), at a homographic elimination step 102.

The computer processes the remaining images in order to identify joint locations 67 and skeleton 69 in each of the remaining images, at a skeleton extraction step 104. As noted earlier, the step can be carried out with the support of a human user, for example, the infant's caregiver, who may select one or more of the images and mark the joint locations on the screen of a client device. The user may scroll through the video sequence in order to find the best frame or frames for this purpose. The computer can then process the other images in the sequence using the cues input by the user. Alternatively or additionally, the computer may extract the skeleton autonomously, using methods of human pose estimation that are known in the art. Deep learning approaches may be effectively applied for this purpose, for example as described by Toshev et al., in "DeepPose: Human Pose Estimation via Deep Neural Networks," which was published in arXiv:1312.4659 and is incorporated herein by reference.

The computer analyzes the infant's pose in each of the images to select one or more image frames in which the infant's pose is appropriate for height measurement and eliminates image frames that are inappropriate, at an invalid pose elimination step 106. For example, the computer may remove images in which the infant is lying on his or her side. The computer measures the infant's height in each of the remaining images, for example by measuring and summing the distances between the joints along the skeleton, at a height extraction step 108.

The height measurements made at step 108 will typically differ from image to image, as the infant moves in the crib. The computer applies decision criteria to the set of height measurements in order to choose and output the measurement that is most likely to be correct, at a height selection step 110. In the embodiment shown in FIG. 7, the computer simply chooses the largest height measurement (after eliminating distant outliers), on the rationale that a pose in which the infant is lying flat with legs straight will give the largest and most correct reading of height. Alternatively, other criteria and estimation techniques can be applied, for example based on statistical analysis of the height measurements.

A pseudocode implementation of a method for infant height measurement is presented in the table below:

TABLE I

INFANT HEIGHT MEASUREMENT

```
s = Selection(frames)
{
   validFrames = { };
   skeletons = { }
   For frame f in frames{
      [valid, s] = extractSkeleton(f);
      If (valid)
         Add s to skeletons;//homography failed or
         //skeleton is in an invalid pose
   }
   Return findBestSkeleton(skeletons);
}
s = findBestSkeleton(skeletons)
{
   best = 0;
   For i = 1 to skeletons.size
      If (skeletons[i].height > skeletons[best].height)
         Best = i;
   Return skeletons[best];
}
```

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for photogrammetric measurement, comprising:
   capturing a sequence of images of an infant lying in a crib, wherein the crib is covered by a bedsheet having a pattern printed thereon;
   processing the images so as to extract a skeleton of the infant from one or more of the images and to identify the pattern in the images; and
   estimating a height of the infant based on the extracted skeleton by computing an image transformation based on the identified pattern and applying the image transformation in estimating the height of the infant.

2. The method according to claim 1, wherein processing the images comprises selecting one or more of the images within the sequence that are appropriate for height measurement, and eliminating the images that are not appropriate.

3. The method according to claim 1, wherein estimating the height comprises measuring and summing distances in the images between joints of the skeleton.

4. The method according to claim 3, wherein estimating the height comprises extracting respective height measurements from a plurality of the images, and outputting a largest value among the height measurements as the height of the infant.

5. The method according to claim 1, wherein applying the image transformation comprises compensating for a scale and a distortion of the images.

6. A computer software product, comprising a non-transitory computer-readable medium in which program instructions are stored, which instructions, when read by a computer, cause the computer to capture a sequence of images of an infant lying in a crib, which is covered by a bedsheet having a pattern printed thereon, to process the images so as to extract a skeleton of the infant from one or more of the images and to identify the pattern in the images, to compute an image transformation based on the identified pattern, and to apply the image transformation in estimating a height of the infant based on the extracted skeleton.

7. The product according to claim 6, wherein the instructions cause the computer to select one or more of the images within the sequence that are appropriate for height measurement, and to eliminate the images that are not appropriate.

8. The product according to claim 6, wherein the instructions cause the computer to estimate the height by measuring and summing distances in the images between joints of the skeleton.

9. The product according to claim 8, wherein the instructions cause the computer to extract respective height measurements from a plurality of the images, and to output a largest value among the height measurements as the height of the infant.

10. The product according to claim 6, wherein the image transformation compensates for a scale and a distortion of the images.

11. A system for photogrammetric measurement, comprising:
 a camera configured to capture a sequence of images of an infant lying in a crib, which is covered by a bedsheet having a pattern printed thereon; and
 a processor, which is configured to process the images so as to extract a skeleton of the infant from one or more of the images and to identify the pattern in the images, to compute an image transformation based on the identified pattern, and to apply the image transformation in estimating a height of the infant based on the extracted skeleton.

12. The system according to claim 11, wherein the processor is configured to select one or more of the images within the sequence that are appropriate for height measurement, and to eliminate the images that are not appropriate.

13. The system according to claim 11, wherein the processor is configured to estimate the height by measuring and summing distances in the images between joints of the skeleton.

14. The system according to claim 13, wherein the processor is configured to extract respective height measurements from a plurality of the images, and to output a largest value among the height measurements as the height of the infant.

15. The system according to claim 11, wherein the image transformation compensates for a scale and a distortion of the images.

* * * * *